United States Patent [19]

Schenk

[11] Patent Number: 4,474,687

[45] Date of Patent: Oct. 2, 1984

[54] ODORANTS CONTAINING ESTERS OF 2,3,6,6-TETRAMETHYLCYCLOHEXENYL CARBOXYLIC ACIDS

[75] Inventor: Hanspeter Schenk, Zumikon, Switzerland

[73] Assignee: Givaudan Corporation, Clifton, N.J.

[21] Appl. No.: 415,512

[22] Filed: Sep. 7, 1982

Related U.S. Application Data

[62] Division of Ser. No. 156,432, Jun. 4, 1980, Pat. No. 4,375,001.

[30] Foreign Application Priority Data

Jun. 13, 1979 [CH] Switzerland ........................ 5527/79
Apr. 24, 1980 [CH] Switzerland ........................ 3163/80

[51] Int. Cl.$^3$ .......................... A61K 7/46; C11B 9/00
[52] U.S. Cl. ................................................ 252/522 R
[58] Field of Search .................................... 252/522 R

[56] References Cited

U.S. PATENT DOCUMENTS 4,260,527 4/1981 Trenkle et al. ................ 252/522 R
4,283,561 8/1981 Hagen et al. ............... 252/522 R X
4,283,576 8/1981 Sprecker et al. ........... 252/522 R X
4,313,842 2/1982 Trenkle et al. ............. 252/522 R X

*Primary Examiner*—Helen M. S. Sneed
*Attorney, Agent, or Firm*—Robert F. Tavares

[57] ABSTRACT

Novel esters, of the general formula

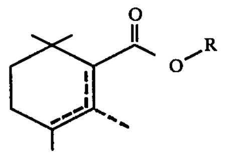

I wherein R represents $C_{1-4}$-alkyl or $C_{2-4}$-alkenyl and one of the three broken lines represents an additional bond, are disclosed. Also disclosed are novel odorant and/or flavoring compositions containing esters of formula I, a process and intermediates for the manufacture of the esters of formula I and the use of esters of formula I as odorant and/or flavoring substances.

5 Claims, No Drawings

ODORANTS CONTAINING ESTERS OF 2,3,6,6-TETRAMETHYLCYCLOHEXENYL CARBOXYLIC ACIDS

This is a division of application Ser. No. 156,432 filed June 4, 1980 now U.S. Pat. No. 4,375,001.

THE INVENTION

The present invention relates to novel odorant and/or flavouring substances. More particularly, the invention is concerned with esters of the general formula

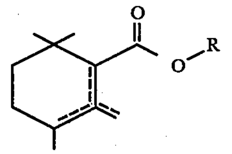

I wherein R represents $C_{1-4}$-alkyl or $C_{2-4}$-alkenyl and one of the three broken lines represents an additional bond.

Formula I is intended to embrace the esters of the formulae

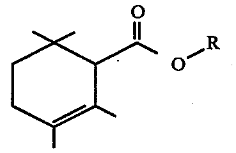

Ia

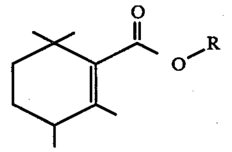

Ib

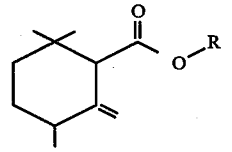

Ic wherein R has the significance given earlier.

The alkyl and alkenyl groups denoted by the symbol R can be straight-chain or branched-chain. Ethyl, isobutyl and allyl are preferred.

The present invention is also concerned with a process for the manufacture of the esters of formula I. This process comprises cyclising an ester of the general formula

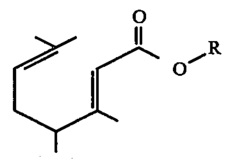

II wherein R has the significance given earlier.

DESCRIPTION OF THE PREFERRED EMBODIMENTS

The manufacture of the esters of formula I can be carried out by cyclizing esters of formula II according to methods similar to those used for the manufacture of cyclogeranyl derivatives.

Suitable cyclisation agents are inorganic and organic protonic acids such as sulphuric acid, phosphoric acid, methanesulphonic acid, formic acid, acetic acid etc. or Lewis acids such as boron trifluoride, tin tetrachloride, zinc chloride etc.

The cyclisation can be carried out in the presence or absence of a solvent. Suitable solvents are inert solvents such as hexane, benzene, nitromethane etc. The temperature is not critical; the cyclisation can be carried out at room temperature or at higher or lower temperatures.

The ester starting materials of formula II are novel. These esters also possess organoleptic properties and are part of the present invention.

The novel esters of formula II are conveniently prepared from the known 3,6-dimethyl-5-hepten-2-one. For example, this ketone can be reacted with a $C_{1-4}$-carbalkoxy-methylenediethylphosphate according to Horner-Wittig reaction [Wadsworth/Emmons modification, J. Amer. Chem. Soc. 83, 1733 (1961)] in the presence of an alkali hydride or alkali alcoholate as the base.

The reaction is conveniently carried out in an aprotic solvent such as benzene, toluene, dimethoxyethane etc. The temperature at which the reaction is carried out is not critical. While a temperature range of ca. 40°–60° C. is preferred, the reaction can also be carried out at a lower or higher temperature.

If desired higher esters of formula II can be prepared from the corresponding methyl or ethyl ester by trans esterification in the customary manner. For example, by heating these lower esters with a higher alcohol (e.g. isobutanol), conveniently under alkaline conditions, the methanol or ethanol formed can be distilled off continuously from the reaction mixture leaving behind the desired higher ester.

According to the process provided by the present invention, the product obtained is an isomer mixture of esters of formulae Ia, Ib and Ic. The compound having formula Ia predominates. When desirable, the separation of the isomer mixture can be carried out in the customary manner; for example, by means of preparative gas chromatography. The organoleptic properties of the different isomers are compatible and it is preferred, on economical grounds, to use a mixture of the isomers.

The esters of formula I possess particular organoleptic properties, on the basis of which they are excellently suited as odorant and/or flavouring substances. The invention is therefore also concerned with the use of the esters of formula I as odorant and/or flavouring substances.

On the basis of their natural odour notes, the esters of formula I are especially suitable for the modification of known compositions where, for example, the citrus notes are to be intensified (e.g. for Cologne types and the like, extracts), also of flowery, especially rose, compositions where, inter alia, the use of esters of formula I leads to a clarification of the musk effect (extract types, compositions of the feminine direction) as well as of woody compositions where the addition of the esters of formula I underlines the sought-after expensive sandal notes (extract types of general direction).

Fruit bases (e.g. of the apricot type) containing esters of formula I are fuller, sweeter and have a pronounced confectionery note.

2,3,6,6-Tetramethyl-2-cyclohexane-1-carboxylic acid ethyl ester, for example, possesses powerful, flowery-spicy as well as woody notes of great radiance. Further, the fruity-sweet, slightly powdery side-notes of this ester are worthy of mention.

This preferred ester differs organoleptically in a clear and surprising manner from the structurally closely related known ester, 2,5,6,6-tetramethyl-cyclohex-2-ene-1-carboxylic acid ethyl ether [H. Favre and H. Schinz, Helv. 35, 1627 (1952)], the latter ester possessing only musty and earthy odour notes.

The esters of formula I combine with numerous known natural or synthetic ingredients of odorant compositions, whereby the range of natural ingredients can embrace not only readily-volatile but also semi-volatile and difficultly-volatile substances, and the range of synthetic ingredients can embrace representations from almost all classes of substances, as will be evident from the following compilation:

Natural products such as tree moss absolute, basil oil, bergamotte oil, acetylated cedarwood oil (e.g. Vertofix-®IFF or Cedartone ®Givaudan), oak moss, galbanum oil, geranium oil, jasmine absolute and its substitute, lavender oil, lavandin oil, mastix absolute, neroli oil, patchouli oil, petitgrain oil Paraguay, sandalwood oil, vetiver oil, ylang-ylang oil, lemon oil and wormwood oil;

alcohols such as linalool, citronellol, geraniol, natural rhodinol, α-terpineol, phenylethyl alcohol, phenylpropyl alcohol and cinnamic alcohol;

aldehydes such as 3,5-dimethyl-cyclohex-3-ene-carboxaldehyde, decanal, methylnonylacetaldehyde, hydroxycitronellal, α-hexylcinnamaldehyde, cyclamen aldehyde, p-tert.butyl-α-methyl-dihydro-cinnamaldehyde (e.g. Lilial ®Givaudan) and citral;

ketones such as α-ionone, acetylcedrene, p-methylacetophenone and methyl ionone;

esters such as cedryl acetate, cis-3-hexenyl acetate, cis-3-hexenyl benzoate, ethyl acetoacetate, linalyl acetate, geranyl acetate, terpenyl acetate, phenylethyl acetate, styrallyl acetate, p-tert.butylcyclohexyl acetate, 4-[4-methyl-3-pentenyl]-cyclohex-3-en-1-yl-carbinyl acetate (Myraldyl acetate ®Givaudan), cinnamyl formate, benzyl acetate, benzyl salicylate, amyl salicylate and methyl dihydrojasmonate;

lactones such as γ-undecalactone and coumarin;

various additional substances often used in perfumery such as musk compounds [musk ambrette, musk ketone, 12-oxa-hexadecanolide (e.g. Musk 174 ®Naarden), 1,1-dimethyl-4-acetyl-6-tert.butylindene, indole], p-menthane-8-thiol-3-one, eugenol, acetaldehyde-propylphenyl-ethyl acetal and methyl 1-methylcyclododecyl ether (e.g. Madrox ®Givaudan).

As flavouring substances, the esters of formula I can be used, for example, for the production, improvement, intensification, enhancement or modification of fruit flavours of various types (e.g. raspberry or apricot flavours). Surprisingly, for example, in grape flavours the characteristic note of fresh grapes can advantageously be emphasized. Fields of application for these flavours include foodstuffs (yoghurt, sweet goods etc), luxury consumables (tea, tobacco etc) and drinks (lemonades etc).

Finally, an especially surprising and valuable finding in accordance with the present invention is the fact that the esters of formula I in combination with an ester of the general formula

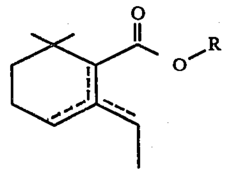

IV wherein R has the significance given earlier and one of the three broken lines represents an additional bond, or with a mixture of esters of formula IV, especially a mixture of an ester of formula I in which R represents ethyl (esters I') with 2-ethyl-6,6-dimethyl-2-cyclohex-ene-1-carboxylic acid ethyl ester (see, for example, DT-OS No. 2644762) have surprising olfactory qualities, namely a great naturalness and radiance. These mixtures accordingly represent a further aspect of the present invention.

The significance of the novel mixtures lies above all in their widespread application. Interesting effects can be achieved especially in flowery bases (specifically those of the rose type), in green bases and fruit bases as well as in compositions of the Eau de Cologne type.

The novel mixtures are likewise particularly suitable for use in fruit flavours of various types, but especially for the flavouring of tobacco.

The ratio of ester of formula I to ester of formula IV can be varied in wide ranges; for example, from 90:10 to 10:90. A range of 10:90 to 30:70 is preferred.

The (extreme) values can readily be adjusted especially by the appropriate choice of the synthesis of the starting material, as will be readily evident from the following Formula Scheme:

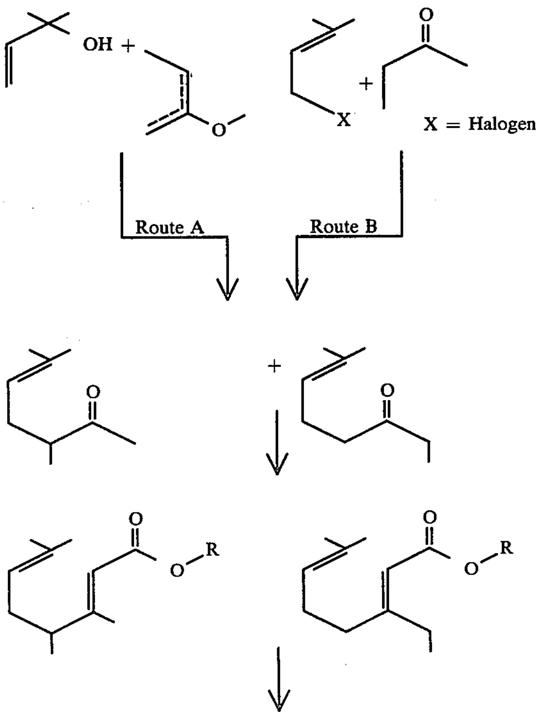

-continued

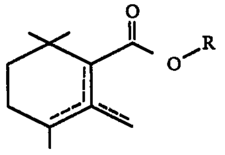

I

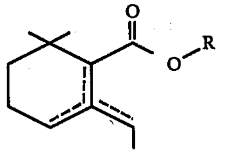

IV

| | |
|---|---|
| Route A: ca 25% I | ca 75% IV |
| Route B: ca 85% I | ca 15% IV |

Both of the routes depicted in the foregoing Formula Scheme for the preparation of the 3,6-dimethyl-5-hepten-2-one/7-methyl-6-octen-3-one mixture are known from the literature [see, for example, Belgian Patent Specification No. 634,738 for Route A, and H. O. House, Modern Synthetic Reactions, W. A. Benjamin Inc., New York 1972 and J. U. Nef, Ann. 310, 318 (1900) for Route B].

According to the foregoing Formula Scheme, esters of formulae I and IV occur as isomer mixtures in which the α-form predominates to a large extent.

The esters of formula I (or the mixtures of esters of formulae I and IV) can be used in wide limits which, for example, can extend from 0.1% in the case of detergents to 30% in the case of alcoholic solutions. It will be appreciated that these values are not limiting values, since the experienced perfumer can also achieve effects with lower concentrations or can synthesise novel complexes with higher concentrations. The preferred concentrations vary between 0.5% and 25%. The compositions produced with esters of formula I can be used for all kinds of perfumed articles (Eau de Cologne, eau de toilette, extracts, lotions, creams, soaps, shampoos, salves, powder, toothpastes, mouth wash, deodorants, detergents, tobacco etc).

The esters of formula I (or the mixtures of esters of formulae I and IV) can accordingly be used in the production of compositions and, as will be evident from the foregoing compilation, using a wide range of known odorant substances or odorant substance mixtures. In the production of such compositions, the known odorant substances or odorant substance mixtures e.g. as specified above can be used according to methods known to the perfumer such as, for example, according to W. A. Poucher, Perfumes, Cosmetics, Soaps 2, 7th Edition, Chapman and Hall, London, 1974.

The pronounced flavour qualities of the esters of formula I (or the mixtures of esters of formulae I and IV) enable them to be used as flavouring substances in low concentrations. A suitable range is, for example, from 0.01 ppm–100 ppm, preferably 0.01 ppm–20 ppm, in the finished product (i.e. the flavoured foodstuff, luxury consumable or drink).

In the flavouring of, for example, tobacco, the concentration can, however, also be higher and can have a wider range; for example, a range of 1 ppm–1000 ppm, preferably 50–500 ppm.

The esters can be mixed with the ingredients used for flavouring compositions or added to such flavourants in the usual manner. Among the flavourants contemplated in accordance with the present invention there are to be understood flavouring compositions which can be diluted or dispersed in edible materials in a manner known per se. They contain, for example, about 0.1–10 weight %, especially 0.5–3 weight %. They can be converted according to methods known per se into the usual forms of use such as solutions, pastes or powders. The products can be spray-dried, vacuum-dried or lyophilised.

The known flavouring substances which are conveniently used in the production of such flavourants are either referred to in the foregoing compilation or can be concluded from the relevant literature (see, for example, J. Merory, Food Flavorings, Composition, Manufacture and Use, Second Edition, The Avi Publishing Company, Inc., Westport, Conn., 1968, or G. Fenaroli, Fenaroli's Handbook of Flavor Ingredients, Second Edition, Volume 2, CRC Press Inc., Cleveland, Ohio 1975).

For the production of the usual forms of use there can be used, for example, the following carrier materials, thickening agents, flavour-improvers, spices and auxiliary ingredients etc:

Gum arabic, tragacanth, salts or brewers' yeast, alginates, carrageen or similar absorbents; indoles, maltol, dienals, spice oleoresins, smoke flavours; cloves, diacetyl, sodium citrate; monosodium glutamate, disodium inosine-5'-monophosphate (IMP), disodium guanosine-5-phosphate (GMP); or special flavouring substances, water, ethanol, propyleneglycol, glycerine.

The following Examples illustrate the present invention:

EXAMPLE 1

228 ml of formic acid are cooled to 0°–5° C. At this temperature there are added 12 ml of concentrated sulphuric acid and subsequently the mixture is stirred for 1 hour. To the resulting acid mixture are cautiously added dropwise at +5° C. 24 g (0.114 mol) of c,t-3,4,7-trimethyl-2,6-octadienoic acid ethyl ester. After completion of the addition, the mixture is left to come to room temperature and it is stirred at this temperature for a further 1 hour. The mixture is poured on to ice and extracted three times with hexane. The combined hexane solutions are washed neutral once with water, twice with sodium bicarbonate solution and finally twice with water, dried over sodium sulphate and evaporated. The crude product (22.5 g) is fractionally distilled in a high vacuum on a 10 cm Widmer column. There are obtained 17 g (70.8%) of 2,3,6,6-tetramethyl-2-cyclohexene-1-carboxylic acid ethyl ester of boiling point 55° C./0.07 mm Hg; $n_D^{20}=1.4640$. According to gas chromatography (glass capillary column, 50 m, UCON HB 5100, 110° C., isothermal, carrier gas helium 2.0 ml/minute), the product has the following composition: ca 91.5% 2,3,6,6-tetramethyl-2-cyclohexene-1-carboxylic acid ethyl ester (relative retention 1.00), ca 9% 2-methylene-3,6,6-trimethylcyclohexane-1-carboxylic acid ethyl ester (cis/trans-isomers, relative retention 1.01 and 1.06) and ca 0.5% 2,3,6,6-tetramethyl-1-cyclohexene-1-carboxylic acid ethyl ester (relative retention 1.12). Spectral data of the main product:

IR (liquid): Band at 1,735 $cm^{-1}$ (C=O, ester).

NMR ($CHCl_3$):

0.9 s (6H) 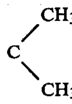

1.26 t/7 (3H) 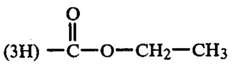

-continued

| | |
|---|---|
| 1.60 m (6H) | $=\overset{\vert}{C}_2-CH_3$ und $=\overset{\vert}{C}_3-CH_3$ |
| 1.95 m (2H) | $-\overset{\vert}{\underset{\vert}{C}}C-CH_2-CH_2-C=$ |
| 2.57 s (1H) | $CH-\overset{O}{\overset{\Vert}{C}}-$ |
| 4.15 q/7 (2H) | $-\overset{O}{\overset{\Vert}{C}}-CH_2-CH_3$ |

MS: 210(M, 11), 137(100), 136(42), 95(24), 121(22) and 81(10).

The c,t-3,4,7-trimethyl-2,6-octadienoic acid ethyl ester used as the starting material can be prepared as follows:

To a cooled solution of 5.8 g (0.252 g atom) of sodium in 130 ml of absolute ethanol is added dropwise at a temperature of 5°–10° C. a solution of 30 g (0.214 mol) of 3,6-dimethyl-5-hepten-2-one and 62.4 g (0.278 mol) of phosphonoacetic acid triethyl ester in 130 ml of absolute toluene. Subsequently, the mixture is left to come to room temperature and to react-out overnight. The mixture is poured on to ice/water and extracted three times with hexane. The combined hexane solutions are washed neutral with sodium chloride solution, dried over sodium sulphate and evaporated. The crude product (43 g) is fractionally distilled in a high vacuum over a 10 cm Widmer column. There are obtained 28.9 g (64.3%) of c,t-3,4,7-trimethyl-2,6-octadienoic acid ethyl ester of boiling point 67°–72° C./0.035 mm Hg; $n_D^{20}=1.4690$.

EXAMPLE 2

According to the procedure described in Example 1, 88.7 g of crude product are obtained in an analogous manner from 90 g of an ester mixture consisting of 75% c,t-3-ethyl-7-methyl-2,6-octadienoic acid ethyl ester and 25% c,t-3,4,7-trimethyl-2,6-octadienoic acid ethyl ester. After fractional distillation in a water-jet vacuum on a 10 cm Widmer column, there are obtained 74.4 g (82.7% of theory) of a mixture consisting of 75% 2-ethyl-6,6-dimethyl-2-cyclohexene-1-carboxylic acid ethyl ester and 25% 2,3,6,6-tetramethyl-2-cyclohexene-1-carboxylic acid ethyl ester of boiling point 102° C./6 mm Hg; $n_D^{20}=1.4626$.

EXAMPLE 3

According to the process described in Example 1, 66.5 g of crude product are obtained in an analogous manner from 71 g of an ester mixture consisting of 80% c,t-3,4,7-trimethyl-2,6-octadienoic acid ethyl ester and 20% c,t-3-ethyl-7-methyl-2,6-octadienoic acid ethyl ester. After fractional distillation in a high vacuum on a 20 cm Widmer column, there are obtained 59.6 g (83.9% of theory) of a mixture consisting of 80% 2,3,6,6-tetramethyl-2-cyclohexene-1-carboxylic acid ethyl ester and 20% 2-ethyl-6,6-dimethyl-2-cyclohexene-1-carboxylic acid ethyl ester of boiling point 64°–66° C./0.01 mm Hg; $n_D^{20}=1.4610$.

EXAMPLE 4

204 ml of formic acid are cooled to 0°–5° C. At this temperature there are added 11 ml of concentrated sulphuric acid and the mixture is stirred for 1 hour. At the same temperature there are added dropwise 20 g (0.102 mol) of a mixture consisting of 77.1% c,t-3-ethyl-7-methyl-2,6-octadienoic acid methyl ester and 22.4% of c,t-3,4,7-trimethyl-2-6-octadienoic acid methyl ester. The mixture is left to come to room temperature and to react-out for 1 hour. The mixture is poured on to ice and extracted three times with hexane. The combined hexane solutions are washed neutral once with water, twice with saturated sodium bicarbonate solution and finally twice with water, dried over sodium sulphate and evaporated. The crude product (19.5 g) is fractionally distilled in a high vacuum on a 15 cm Widmer column. There are obtained 15.5 g (77.5%) of a mixture of boiling point 38°–41° C./0.05 mm Hg; $n_D^{20}=1.4650$. According to gas chromatography (glass capillary column 60 m×0.3 mm i.d. with Ucon HB 5100, 70°–185° C. with 3.0° C./minute, helium flow 2.5 ml/minute), the product has the following composition: 20.2% 2,3,6,6-tetramethyl-2-cyclohexene-1-carboxylic acid methyl ester and 73.4% 2-ethyl-6,6-dimethyl-2-cyclohexene-1-carboxylic acid methyl ester, as well as a small amount of c,t-2-ethylidene-6,6-dimethyl-cyclohexane-1-carboxylic acid methyl ester.

The ester mixture consisting of 77.1% c,t-3-ethyl-7-methyl-2,6-octadienoic acid methyl ester and 22.4% c,t-3,4,7-trimethyl-2,6-octadienoic acid methyl ester used as the starting material can be prepared as follows:

To a solution, cooled to 5° C., of 9.7 g (0.422 mol) of sodium in 220 ml of absolute methanol is added dropwise over a period of 1 hour at this temperature a solution of 85 g (0.467 mol) of phosphonoacetic acid trimethyl ester and 50 g (0.357 mol) of a ketone mixture consisting of 23.9% 3,6-dimethyl-5-hepten-2-one and 76.1% 7-methyl-6-octen-3-one in 220 ml of absolute toluene. Subsequently, the mixture is left to come to room temperature and to react-out overnight. The mixture is poured on to ice and extracted three times with hexane. The combined hexane solutions are washed neutral with sodium chloride solution, dried over sodium sulphate and evaporated. The crude product (81.8 g) is fractionally distilled in a high vacuum over a 15 cm Widmer column. There are obtained 44.8 g (64.0%) of a mixture of boiling point 58°–61° C./0.02 mm Hg; $n_D^{20}=1.4708$. The mixture consists of 77.1% c,t-3-ethyl-7-methyl-2,6-octadienoic acid methyl ester and 22.4% c,t-3,4,7-trimethyl-2,6-octadienoic acid methyl ester.

The ketone mixture consisting of 23.9% 3,6-dimethyl-5-hepten-2-one and 76.1% 7-methyl-6-octen-3-one can be obtained in a manner known per se (see, for example, Belgian Patent Specification No. 634,738 of 10.1.1964) in 54.4% yield from 3-methyl-1-buten-3-ol, methyl butenyl ether and phosphoric acid as the catalyst in an autoclave at 180° C.

EXAMPLE 5

155 ml of formic acid are cooled to 0°–5° C. At this temperature there are added 15.5 ml of concentrated sulphuric acid and subsequently the mixture is stirred for 1 hour. At the same temperature there is added dropwise a solution of 24.5 g (0.103 mol) of a mixture of 71.6% c,t-3-ethyl-7-methyl-2,6-octadienoic acid isobutyl ester and 20.1% c,t-3,4,7-trimethyl-2,6-octadienoic acid isobutyl ester in 50 ml of hexane. The mixture is left to come to room temperature and to react-out for 1 hour. The mixture is poured on to ice and extracted three times with hexane. The combined hexane solutions are washed neutral once with water, twice with saturated sodium bicarbonate solution and finally twice with water, dried over sodium sulphate and evaporated. The crude product (21.2 g) is fractionally distilled in a high vacuum on a 15 cm Widmer column. There are obtained 16.9 g (69.0%) of a mixture of boiling point 64°-66° C./0.04 mm Hg; $n_D^{20}=1.4608$.

According to gas chromatography (glass capillary column 50 m×0.3 mm i.d. with Ucon HB 5100, 70°-185° C. with 3.0° C./minute, helium flow 2.5 ml/minute), the product has the following composition: 12.7% c,t-2-ethylidene-6,6-dimethyl-cyclohexane-1-carboxylic acid isobutyl ester, 19.9% 2,3,6,6-tetramethyl-2-cyclohexene-1-carboxylic acid isobutyl ester and 60.1% 2-ethyl-6,6-dimethyl-2-cyclohexene-1-carboxylic acid isobutyl ester.

The ester mixture consisting of 71.6% c,t-3-ethyl-7-methyl-2,6-octadienoic acid isobutyl ester and 20.1% c,t-3,4,7-trimethyl-2,6-octadienoic acid isobutyl ester used as the starting material can be prepared as follows:

140 mg (6.1 mmol) of sodium are dissolved in 100 g of isobutanol under a nitrogen atmosphere and while warming. At room temperature there is added dropwise a solution of 27 g (0.138 mol) of a mixture consisting of 77.1% c,t-3-ethyl-7-methyl-2,6-octadienoic acid methyl ester and 22.4% c,t-3,4,7-trimethyl-2,6-octadienoic acid methyl ester in 200 ml of cyclohexene. Subsequently, ca 150 ml of cyclohexane are distilled off continuously over a 15 cm Vigreux column in ca 4 hours. Simultaneously, the distilled-off amount of cyclohexane is continuously replaced from a dropping funnel. The solution is subsequently poured on to ice and washed neutral once with saturated sodium bicarbonate solution and twice with water. After drying over sodium sulphate and concentration on a rotary evaporator, there remain behind 29.4 g of crude product. A fractional distillation in a high vacuum over a 15 cm Widmer column gives 23.3 g (71.0%) of a mixture of boiling point 77°-80° C./0.04 mm Hg; $n_D^{20}=1.4660$. The mixture consists of 71.6% c,t-3-ethyl-7-methyl-2,6-octadienoic acid isobutyl ester and 20.1% c,t-3,4,7-trimethyl-2,6-octadienoic acid isobutyl ester.

EXAMPLE 6

35 ml of formic acid are cooled to 0°-5° C. At this temperature there are added 3.5 ml of concentrated sulphuric acid and subsequently the mixture is stirred for 1 hour. At the same temperature there is added dropwise a solution of 5.2 g (23.4 mmol) of a mixture consisting of 83.8% c,t-3-ethyl-7-methyl-2,6-octadienoic acid allyl ester and 9.1% c,t-3,4,7-trimethyl-2,6-octadienoic acid allyl ester in 15 ml of hexane. The mixture is left to come to room temperature and is stirred for 1.5 hours. The mixture is poured on to ice and extracted twice with hexane. The combined hexane solutions are washed neutral once with water, twice with saturated sodium bicarbonate solution and finally twice with water, dried over sodium sulphate and evaporated. The crude product (3.9 g) is distilled in a bulb-tone. There are obtained 3.7 g (71.2%) of a mixture of boiling point 110° C./0.05 mm Hg; $n_D^{20}=1.4720$.

According to gas chromatography (glass capillary column 50 m×0.3 mm i.d. with Ucon HB 5100, 70°-185° C. with 3° C./minute, helium flow 2.5 ml/minute), 12.3% c,t-2-ethylidene-6,6-dimethyl-cyclohexane-1-carboxylic acid allyl ester, 7.2% 2,3,6,6-tetramethyl-2-cyclohexene-1-carboxylic acid allyl ester and 67.4% 2-ethyl-6,6-dimethyl-2-cyclohexene-1-carboxylic acid allyl ester.

The ester mixture consisting of 83.8% c,t-3-ethyl-7-methyl-2,6-octadienoic acid allyl ester and 9.1% c,t-3,4,7-trimethyl-2,6-octadienoic acid allyl ester used as the starting material can be prepared as follows:

250 mg (10.8 mmol) of sodium are dissolved in 145 g of allyl alcohol under a nitrogen atmosphere and while warming. At room temperature there is added dropwise a solution of 49 g (0.25 mol) of a mixture consisting of 86.5% c,t-3-ethyl-7-methyl-2,6-octadienoic acid methyl ester and 9.5% c,t-3,4,7-trimethyl-2,6-octadienoic acid methyl ester in 250 ml of cyclohexane. 200 ml of cyclohexane are continuously distilled off within 3 hours at a bath temperature of 90° C. over a 15 cm Vigreux column, the distilled-off amount of cyclohexane being continuously replaced from a dropping funnel. The mixture is subsequently poured on to ice and washed neutral once with saturated sodium bicarbonate solution and twice with water. After drying over sodium sulphate and concentration on a rotary evaporator, there remain behind 53.8 g of crude product. A fractional distillation in a high vacuum over a 20 cm Widmer column gives 38.7 g (69.7%) of a mixture of boiling point 92°-94° C./0.08 mm Hg; $n_D^{20}=1.4768$. The mixture consists of 83.8% c,t-3-ethyl-7-methyl-2-6-octadienoic acid allyl ester and 9.1% c,t-3,4,7-trimethyl-2,6-octadienoic acid allyl ester.

EXAMPLE 7

| Composition (chypre) | Parts by weight |
|---|---|
| Styrallyl acetate | 20 |
| Methylnonylacetaldehyde (10% in diethyl phthalate) | 20 |
| Vetiveryl acetate | 50 |
| Rhodinol | 50 |
| Patchouli oil | 50 |
| Tree moss absolute (50% in diethyl phthalate) | 50 |
| p-Tert.butyl-α-methylhydro-cinnamaldehyde | 100 |
| Hydroxycitronellal | 100 |
| Methyl ionone | 100 |
| Musk ambrette | 100 |
| Coumarin | 100 |
| Bergamotte oil | 100 |
| | 840 |

By the addition of 16% of the ethyl ester of formula I (I') the methylnonylacetaldehyde in the composition is very pleasantly underlined, the base becomes altogether lighter and there is thus produced, by the addition of the novel ester, a composition having a novel direction for the well-known chypre range.

EXAMPLE 8

| Composition (woody type) | Parts by weight |
|---|---|
| Basil oil | 30 |
| Methyl ionone | 50 |
| p-Tert.butylcyclohexyl acetate | 50 |
| Methyl dihydrojasmonate | 70 |
| Cedryl acetate (crystalline) | 100 |
| Sandalwood oil | 200 |

-continued

| Composition (woody type) | Parts by weight |
|---|---|
| Patchouli oil | 200 |
| Bergamotte oil | 200 |
| | 900 |

Addition of 100 parts of the ester I' leads to a clear underlining of the sandalwood note.

A really surprising result can be achieved by the addition of the same amount of the ester mixture I' and IV' (in the ratio 10:90 to 30:70). This addition confers to the generally woody composition a very elegant note which, in the production of simple compositions, sets the stamp of a practically complete composition "mens lines".

EXAMPLE 9

| Composition (Cologne type) | Parts by weight |
|---|---|
| Indole (10%) | 10 |
| Coumarin | 10 |
| Ylang-ylang oil | 20 |
| Neroli oil | 40 |
| Lavandin oil | 40 |
| Benzyl acetate | 40 |
| Eugenol (extra) | 40 |
| Citral | 60 |
| Methyl dihydrojasmonate | 100 |
| α-Hexylcinnamaldehyde | 100 |
| Lemon oil (Italian) | 100 |
| Bergamotte oil | 360 |
| | 920 |

Addition of 80 parts of the ester I' confer to this generally Cologne type a stronger perceptible lemon effect which is distinguished especially by freshness.

A still better effect can be achieved by the addition of the ester mixture I' and IV' (15:85), since this confers not only freshness but also character and at the same time improves the original "simple" acting Cologne type in a very pleasing manner.

EXAMPLE 10

| Green base | Parts by weight |
|---|---|
| Citral | 10 |
| Wormwood oil | 10 |
| Mastix absolute | 20 |
| Basil oil | 80 |
| Methyl dihydrojasmonate | 100 |
| Alcohol (95°) | 130 |
| Linalyl acetate | 200 |
| α-Hexylcinnamaldehyde | 200 |
| Benzyl salicylate | 200 |
| | 950 |

Addition of 50 parts of the ester I' underlines the influence of the wormwood oil in this composition in a noteworthy manner, while ester IV' in contrast thereto emphasises the mastix absolute with its typical green note.

The combined effect of an ester mixture I' and IV' (15:85) shows, however, surprising results. Neither the one slightly bitter note nor the other note are favoured, whereas on the other hand the composition leaves behind a very harmonic total impression with a now fruity note and possesses a considerably increased diffusion. A panel clearly preferred the last-named composition to the other.

EXAMPLE 11

| Perfume composition with flowery character | Parts by weight |
|---|---|
| Laurin (hydroxycitronellal extra) | 760 |
| Linalool | 70 |
| n-Hexyl salicylate | 30 |
| Cyclamen aldehyde | 20 |
| Galbanum oil | 20 |
| | 900 |

This simply prepared flowery complex is altered by the addition of 100 parts of the ester I' in that the influence of the cyclamen aldehyde is repressed. The complex appears substantially fresher and ligher than without this addition. On the other hand, ester IV' underlines the linalool.

If, on the other hand, the same amount of an ester mixture I' and IV' (10:90 to 30:70) is added, then surprisingly the hydroxycitronellal note is underlined. This composition is by far the most powerful and most diffusive and is therefore clearly preferred by an evaluating panel.

EXAMPLE 12

| Composition with rose character | Parts by weight |
|---|---|
| 3,5-Dimethyl-cyclohex-3-ene-carboxaldehyde (10% in propyleneglycol) | 2 |
| n-Decanal (10% in propyleneglycol | 3 |
| Geranyl acetate | 5 |
| α-Ionone | 10 |
| 1,1-Dimethyl-4-acetyl-6-tert.butyl-indane | 10 |
| Cinnamic alcohol (synthetic) | 50 |
| Citronellol (extra) | 100 |
| Geranil (extra) | 200 |
| Phenylethyl alcohol (extra) | 500 |
| | 880 |

By the addition of 12% of the ester I' the base takes on a very pronounced musk character. With reference to its flowery character, this is reminiscent of a pale rose. By the addition of 12% of ester IV' the musk character can not be produced; on the other hand the olfactory character of dark rose (damask rose) is generated.

By the addition of 12% of the ester mixture I' and IV' (15:85) the olfactory character of the original base is quite substantially improved, only an addition of the ester mixture I' and IV' improves in the direction of a slightly fruity, pleasantly fresh dog rose.

EXAMPLE 13

| Tobacco flavour (top flavour, for example for cigarettes) | Parts by weight | |
|---|---|---|
| | A | B |
| p-Cymene | 1.0 | 1.0 |
| Camphor | 2.5 | 2.5 |
| α-Terpineol | 3.5 | 3.5 |
| Ethyl phenylacetate | 4.0 | 4.0 |
| d-Limonene | 5.0 | 5.0 |

-continued

| Tobacco flavour (top flavour, for example for cigarettes) | Parts by weight | |
|---|---|---|
| | A | B |
| β-Ionone | 8.0 | 8.0 |
| Furfural | 10.0 | 10.0 |
| Linalool oxide | 10.0 | 10.0 |
| Phenylethyl alcohol | 20.0 | 20.0 |
| Phenylacetic acid | 20.0 | 20.0 |
| Linalool | 20.0 | 20.0 |
| Cis-jasmone | 20.0 | 20.0 |
| Vanillin | 30.0 | 30.0 |
| Menthol | 30.0 | 30.0 |
| Tetramethylpyrazine | 30.0 | 30.0 |
| Benzaldehyde | 40.0 | 40.0 |
| β-Caryophyllene | 40.0 | 40.0 |
| Ester mixture I' and IV' | — | 10.0 |
| Alcohol (denatured) | 706.0 | 696.0 |
| | 1000.0 | 1000.0 |

The suitable concentration amounts, for example, to 100 g of flavour per 100 kg of tobacco. By the addition of the ester mixture I' and IV' (in the ration 25:75) to composition A the tobacco note is significantly strengthened. When the flavoured tobacco is smoked, there results a typical olfactory flavour impression which is strongly reminiscent of blond Virginia tobacco.

EXAMPLE 14

| Raspberry flavour | Parts by weight | |
|---|---|---|
| | A | B |
| Anisyl formate | 0.2 | 0.2 |
| Methyl-isoeugenol | 0.2 | 0.2 |
| Bornyl acetate (1% in alcohol) | 0.25 | 0.25 |
| Vanillin | 0.25 | 0.25 |
| Iris Concrete (10% in alcohol) | 0.4 | 0.4 |
| β-Ionone | 0.4 | 0.4 |
| Acetylmethylcarbinol (1% in alcohol) | 0.65 | 0.65 |
| Piperonyl acetate | 1.0 | 1.0 |
| α-Ionone | 1.25 | 1.25 |
| Ethyl valerate | 2.0 | 2.0 |
| Dimethylsulphide (10% in alcohol) | 4.0 | 4.0 |
| Leaf alcohol | 5.0 | 5.0 |
| n-Amyl alcohol | 5.0 | 5.0 |
| Ethyl butyrate | 5.0 | 5.0 |
| α-Terpineol | 5.0 | 5.0 |
| Ethylmaltol | 5.0 | 5.0 |
| Isobutyric acid | 10.0 | 10.0 |
| Raspberry ketone | 12.0 | 12.0 |
| Benzyl alcohol | 17.4 | 17.4 |
| Ethyl acetate | 25.0 | 25.0 |
| Ethanol | 900.0 | 890.0 |
| Ester mixture I' and IV' | — | 10.0 |
| | 1000.0 | 1000.0 |

The suitable concentration amounts, for example, to 40 g in 100 liters of syrup. By the addition of the ester mixture 1' and IV' (in the ratio 25:75) to composition A the original note which is fruity regarding smell and taste is clearly strengthened. In both cases there can be detected a novel note which is reminiscent of fresh raspberries.

EXAMPLE 15

| Grape flavour | Parts by weight | |
|---|---|---|
| | A | B |
| Ethyl isovalerate | 10.0 | 10.0 |
| Cinnamic alcohol | 10.0 | 10.0 |
| Citral (10% in alcohol) | 10.0 | 10.0 |
| C—16-aldehyde (10% in alcohol) | 10.0 | 10.0 |
| Ethyl oenanthate | 10.0 | 10.0 |
| Petitgrain oil (10% in alcohol) | 10.0 | 10.0 |
| Rum ether | 10.0 | 10.0 |
| Maltol | 10.0 | 10.0 |
| Benzaldehyde (10% in alcohol) | 15.0 | 15.0 |
| Raspberry ketone | 20.0 | 20.0 |
| Ethyl butyrate | 20.0 | 20.0 |
| Methyl anthranilate | 40.0 | 40.0 |
| Ethyl acetate | 50.0 | 50.0 |
| Ethanol | 775.0 | 725.0 |
| Ester mixture I' and IV' (10% in alcohol) | — | 50.0 |
| | 1000.0 | 1000.0 |

A suitable concentration amounts, for example, to 40 g of flavour in 100 liters of syrup. By the addition of the ester mixture I' and IV' (in the ration 25:75) to composition A there occurs, regarding odour and flavour, a clearly detectable alteration. Regarding flavour, the originally present sweet note is advantageously softened and there newly appears a fruity-fresh note which is characteristic of fresh grapes.

I claim:

1. An odorant composition comprising an olfactorily effective amount of an ester of the general formula

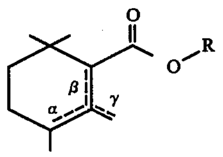

wherein R represents $C_{1-4}$-alkyl or $C_{2-4}$-alkenyl and one of the three broken lines represents an additional bond.

2. An odorant composition according to claim 1 wherein R represents ethyl.

3. An odorant composition according to claim 2 wherein there is an olfactorily effective amount of a mixture which consists essentially of 85–100% of 2,3,6,6-tetramethyl-2-cyclohexene-1-carboxylic acid ethyl ester; 0–5% of 2,3,6,6-tetramethyl-1-cyclohexene-1-carboxylic acid ethyl ester and 0–15% of 2-methylene-3,6,6-trimethylcyclohexane-1-carboxylic acid ethyl ester.

4. An odorant composition according to claim 2 which contains 2,3,6,6-tetramethyl-2-cyclohexene-1-carboxylic acid ethyl ester.

5. An odorant composition according to claims 2, 3 or 4 wherein there is present an olfactorily effective amount of 2-ethyl-6,6-dimethyl-2-cyclohexene-1-carboxylic acid ethyl ester.

* * * * *